United States Patent [19]

Serban et al.

[11] Patent Number: 4,511,391
[45] Date of Patent: Apr. 16, 1985

[54] CYCLOHEXANE-1,3-DIONE DERIVATIVES AND THEIR HERBICIDAL COMPOSITIONS AND METHODS

[75] Inventors: Alexander Serban, Doncaster; Keith G. Watson, Box Hill North; Graham J. Bird, North Melbourne; Graeme J. Farquharson, Reservoir, all of Australia

[73] Assignee: ICI Australia Limited, Melbourne, Australia

[21] Appl. No.: 497,683

[22] Filed: May 24, 1983

[30] Foreign Application Priority Data

May 24, 1983 [AU] Australia ............... PF4118

[51] Int. Cl.³ .................. A01N 43/12; C07D 307/78
[52] U.S. Cl. ........................................ 71/88; 71/90;
549/10; 549/11; 549/15; 549/23; 549/32;
549/51; 549/57; 549/58; 549/60; 549/350;
549/355; 549/362; 549/398; 549/404; 549/405;
549/408; 549/436; 549/438; 549/439; 549/442;
549/462
[58] Field of Search ............ 549/462, 10, 11, 15,
549/23, 32, 51, 57, 58, 350, 355, 398, 438, 362,
404, 405, 408, 436, 439, 442, 60; 71/88, 90

[56] References Cited
U.S. PATENT DOCUMENTS 3,950,420  4/1976  Sawaki et al. .................. 546/256

FOREIGN PATENT DOCUMENTS 1481389  7/1977  United Kingdom .
0017195 10/1980  United Kingdom .

OTHER PUBLICATIONS

Chemical Abstracts, vol. 86, No. 3, Jan. 17, 1977, p. 397, No. 16357h, Columbus, Ohio, USA & JP-A-76 76245, (Nippon Soda Co., Ltd), 01/07/1976.

Primary Examiner—Henry R. Jiles
Assistant Examiner—Bernard I. Dentz
Attorney, Agent, or Firm—Cushman, Darby & Cushman

[57] ABSTRACT

The invention concerns novel compounds of the formula I

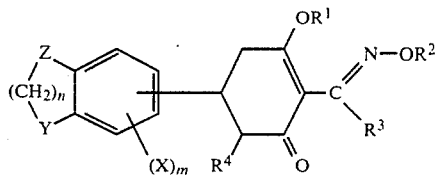

wherein:
X is selected from halogen, nitro, cyano, alkyl, substituted alkyl, alkenyl, alkynyl, hydroxy, alkoxy, substituted alkoxy, alkenyloxy, alkynyloxy, alkanoyloxy, alkoxycarbonyl, alkylthio, alkylsulfinyl, alkylsulfonyl, sulfamoyl, substituted sulfamoyl, benzyloxy, substituted benzyloxy, amino, substituted amino, and the groups formyl and alkanoyl and the oxime, imine and Schiff base derivatives thereof;
Y and Z are independently selected from methylene, oxygen and sulfur provided that at least one of Y and Z is selected from oxygen and sulfur;
$R^1$ is selected from hydrogen, alkyl, alkenyl alkynyl, substituted alkyl, acyl, alkylsulfonyl, benzenesulfonyl, substituted benzenesulfonyl, and an inorganic or organic cation;
$R^2$ is selected from alkyl, alkenyl, alkynyl, substituted alkyl, haloalkenyl and haloalkynyl;
$R^3$ is selected from alkyl, fluoroalkyl, alkenyl, alkynyl and phenyl;
$R^4$ is selected from hydrogen, halogen, cyano, $C_1$ to $C_6$ alkyl and ($C_1$ to $C_6$ alkoxy)carbonyl;
n is an integer selected from 1 to 3; and
m is zero or an integer selected from 1 to 3.

The compounds are cereal selective herbicides and in further embodiments the invention provides processes for the preparation of compounds of formula I, intermediates useful in the preparation of compounds of formula I, intermediates useful in the preparation of compounds of formula I, herbicidal compositions containing as active ingredient a compound of formula I, and processes for severely damaging or killing unwanted plants by applying to the plants or to the growth medium of the plants an effective amount of a compound of formula I.

12 Claims, No Drawings

CYCLOHEXANE-1,3-DIONE DERIVATIVES AND THEIR HERBICIDAL COMPOSITIONS AND METHODS

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes utilizing such compounds.

The use of certain cyclohexane-1,3-dione derivatives as grass herbicides is known in the art. For example, the "Pesticide Manual" (C. R. Worthing Editor, The British Crop Protection Council, 6th Edition 1979) describes the cyclohexane-1,3-dione derivative known commercially as alloxydim-sodium(methyl 3-[1-allyloxyimino)butyl]-4-hydroxy-6,6-dimethyl-2-oxocyclohex-3-ene-carboxylate) and its use as a grass herbicide. This compound is disclosed in Australian Patent No. 464 655 and its equivalents such as UK Patent No. 1 461 170 and U.S. Pat. No. 3,950,420.

More recently, at the 1980 British Crop Protection Conference ("1980 British Crop Protection Conference—Weeds, Proceedings Vol 1, Research Reports", pp 39 to 46, British Crop Protection Council, 1980), a new cyclohexane-1,3-dione grass herbicide code name NP 55 (2-(N-ethoxybutrimidoyl)-5-(2-ethylthiopropyl)-3-hydroxy-2-cyclohexen-1-one) was announced. This compound is disclosed in Australian Patent No. 513 917 and its equivalents.

As indicated above, both alloxydim-sodium and NP 55 are grass herbicides, that is, herbicides which selectively control the growth of grass weeds (monocotyledonous plants) in broad-leaved crops (dicotyledonous plants).

At the 1978 International Union of Pure and Applied Chemistry Fourth International Congress of Pesticide Chemistry ("Advances in Pesticide Science—Part 2", pp 235–243, Pergamon Press, 1979) in a paper discussing the chemical structure and herbicidal activity of alloxy-dim sodium, Iwataki and Hirono made the following disclosure about the herbicidal selectivity between wheat and oats of certain 5-phenyl substituted cyclohexane-1,3-dione derivatives:

"When substituted phenyl groups were introduced at the C-5 position (Table 6), the selectivity between wheats and oats such as *Avena fatua* and *Avena sativa* was observed. The selectivity was found only in the case of para-substituents at the phenyl nucleus and the effect was not found in the case of di- or tri-substitution. Even in the para-substituents, the degree of activity or selectivity was different. The best result was obtained when the methyl group was introduced at the para-position and the hydroxy or the methoxy derivative gave moderately good results."

It has now been found that certain novel 5-aryl substituted cyclohexan-1,3-dione derivatives exhibit particularly useful cereal selective herbicidal activity.

Accordingly the invention provides a compound of formula I:

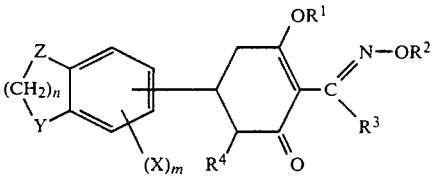

wherein:

X, which may be the same or different, are selected from the group consisting of: halogen; nitro; cyano; $C_1$ to $C_6$ alkyl; $C_1$ to $C_6$ alkyl substituted with a substituent selected from the group consisting of halogen, nitro, hydroxy, $C_1$ to $C_6$ alkoxy and $C_1$ to $C_6$ alkylthio; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkenyloxy; $C_2$ to $C_6$ alkynyloxy; $C_2$ to $C_6$ alkanoyloxy; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, benzoyl and benzyl; the groups formyl and $C_2$ to $C_6$ alkanoyl and the oxime, imine and Schiff base derivatives thereof;

Y and Z are independently selected from methylene, oxygen and sulfur provided that at least one of Y and Z is selected from oxygen and sulfur;

$R^1$ is selected from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; ($C_1$ to $C_6$ alkyl)sulfonyl; benzenesulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation;

$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl;

$R^4$ is selected from the group consisting of: hydrogen; halogen; cyano; $C_1$ to $C_6$ alkyl; and ($C_1$ to $C_6$ alkoxy)carbonyl;

n is an integer selected from 1 to 3; and m is zero or an integer selected from 1 to 3.

When in the compound of formula I X is selected from the group formyl and $C_2$ to $C_6$ alkanoyl and the oxime, imine and Schiff base derivatives thereof, the nature of the oxime, imine and Schiff base derivatives is not narrowly critical. Although not intending to be bound by theory, it is believed that in the plant the (substituted) imine group may be removed to give the corresponding compound of formula I in which X is formyl or $C_2$ to $C_6$ alkanoyl. Suitable values for the groups formyl and $C_2$ to $C_6$ alkanoyl and the oxime, imine and Schiff base derivatives thereof include groups of the formula $-C(R^7)=NR^8$ wherein $R^7$ is selected from hydrogen and $C_1$ to $C_5$ alkyl and $R^8$ is selected from hydrogen, $C_1$ to $C_6$ alkyl, phenyl, benzyl, hydroxy, $C_1$ to $C_6$ alkoxy, phenoxy and benzyloxy.

When in the compound of formula I $R^1$ is selected from acyl the nature of the acyl group is not narrowly critical. Although not intending to be bound by theory, it is believed that when $R^1$ is acyl the acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and heteroaroyl, for example 2-furoyl, 3-furoyl, 2-thenoyl and 3-thenoyl.

When in the compound of formula I $R^1$ is selected from an inorganic or organic cation the nature of the cation is not narrowly critical. Although not intending to be bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^9R^{10}R^{11}R^{12}N^{\oplus}$ wherein $R^9$, $R^{10}$, $R^{11}$ and $R^{12}$ are independently selected from the group consisting of: hydrogen; $C_1$ to $C_{10}$ alkyl; substituted $C_1$ to $C_{10}$ alkyl wherein the alkyl group is substituted with a substituent selected from the group consisting of hydroxy, halogen and $C_1$ to $C_6$ alkoxy; phenyl; benzyl; and the groups substituted phenyl and substituted benzyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R^1$ is hydrogen the compounds of the invention may exist in any one of four tautomeric forms as shown below:

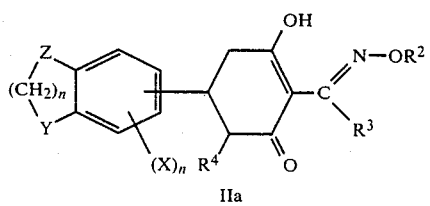

IIa

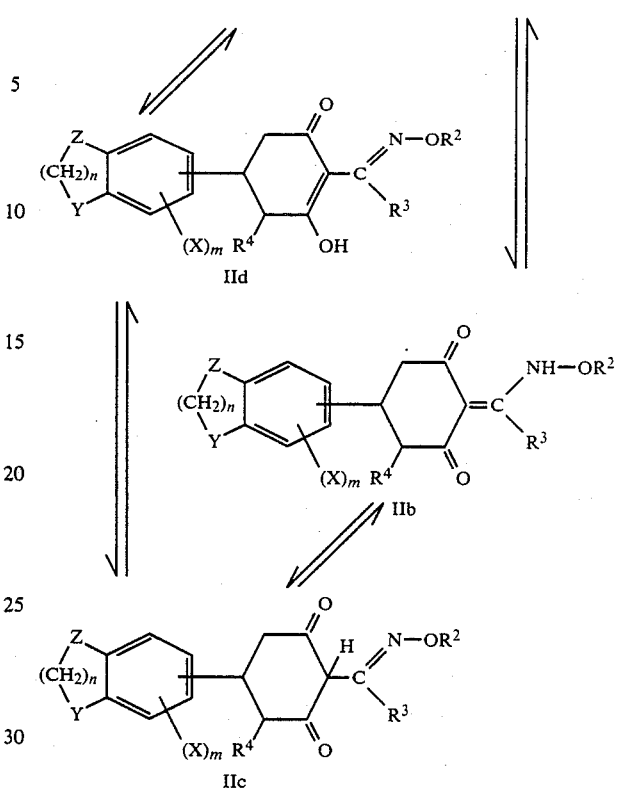

IId

IIb

IIc

Suitable X include: halogen; nitro; cyano; $C_1$ to $C_6$ alkyl, $C_1$ to $C_6$ alkyl substituted with a substituent selected from halogen, nitro and $C_1$ to $C_6$ alkoxy; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkanoyloxy; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, benzoyl and benzyl; and the group $-C(R^7)=NR^8$ wherein $R^7$ is selected from hydrogen and $C_1$ to $C_5$ alkyl and $R^8$ is selected from the group consisting of hydrogen, $C_1$ to $C_6$ alkyl, phenyl, benzyl, hydroxy, $C_1$ to $C_6$ alkoxy, phenoxy and benzyloxy.

Suitable Y and Z include methylene, oxygen and sulfur provided that at least one of Y and Z is selected from oxygen and sulfur.

Suitable $R^1$ include: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl)sulfonyl; benzenesulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_2$ to $C_6$ alkanoyl; benzoyl and substituted benzoyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; 2-furoyl; 3-furoyl; 2-thenoyl; 3-thenoyl; and an inorganic or an organic cation selected from the alkali metal ions, the alkaline earth metal ions, transition metal ions and the ammonium ion $R^9R^{10}R^{11}R^{12}N^\oplus$ wherein $R^9$, $R^{10}$, $R^{11}$ and $R^{12}$ are independently selected from the group consisting of: hydrogen; $C_1$ to $C_{10}$ alkyl; substituted $C_1$ to $C_{10}$ alkyl wherein the alkyl group is substituted with a substituent selected from the group consisting of hydroxy, halogen and $C_1$ to $C_6$ alkoxy; phenyl; benzyl; and the groups substituted phenyl and substituted benzyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

Suitable $R^2$ include: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

Suitable $R^3$ include: $C_1$ to $C_6$ alkyl, $C_1$ to $C_6$ fluoroalkyl; $C_2$ to $C_6$ alkenyl; $C_2$ to $C_6$ alkynyl; and phenyl.

Suitable $R^4$ include hydrogen.

Suitable n include integers selected from 1 to 3.

Suitable m include zero and integers selected from 1 to 3.

Preferred X include: halogen; nitro; cyano; $C_1$ to $C_6$ alkyl; $C_1$ to $C_6$ haloalkyl; $C_1$ to $C_6$ hydroxyalkyl; ($C_1$ to $C_6$ alkoxy) $C_1$ to $C_6$ alkyl; $C_1$ to $C_6$ alkoxy; $C_1$ to $C_6$ alkylthio; $C_1$ to $C_6$ alkylsulfinyl; $C_1$ to $C_6$ alkylsulfonyl; and $C_2$ to $C_6$ alkanoyl.

Preferred $R^1$ include: hydrogen; $C_2$ to $C_6$ alkanoyl such as acetyl and pivaloyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy, benzenesulfonyl and substituted benzenesulfonyl wherein the benzene ring is substituted with from one to three substituents selected from the group consisting of halogen, nitro, $C_1$ to $C_6$ alkyl and $C_1$ to $C_6$ alkoxy; and an inorganic or organic cation selected from the cations of the alkali metals such as lithium, potassium and sodium, the cations of the alkaline earth metals such as magnesium, calcium and barium, the cations of the transition metals such as manganese, copper, zinc, iron, nickel, cobalt and silver, the ammonium ion and the tri- and tetra-(alkyl)ammonium ions wherein alkyl is selected from $C_1$ to $C_6$ alkyl and $C_1$ to $C_6$ hydroxyalkyl.

Preferred $R^2$ include: $C_1$ to $C_6$ alkyl; $C_2$ to $C_6$ alkenyl; $C_2$ to $C_6$ alkynyl; $C_1$ to $C_6$ haloalkyl; $C_2$ to $C_6$ haloalkenyl; and $C_2$ to $C_6$ haloalkynyl.

Preferred $R^3$ include $C_1$ to $C_6$ alkyl.

Preferred $R^4$ include: hydrogen; halogen; cyano; methyl; ethyl; and ($C_1$ to $C_6$ alkoxy)carbonyl.

Preferred n include integers selected from 1 and 2.

More preferred X include: halogen; nitro; cyano; $C_1$ to $C_6$ alkyl; ($C_1$ to $C_6$ alkoxy)methyl; $C_1$ to $C_6$ alkoxy; $C_1$ to $C_6$ alkylthio; and $C_2$ to $C_6$ alkanoyl.

More preferred $R^1$ include: hydrogen; $C_2$ to $C_6$ alkanoyl; benzoyl; benzenesulfonyl; the alkali metal ions; the alkaline earth metal ions; the transition metal ions; the ammonium ion; and the tri- and tetra(alkyl)ammonium ions wherein alkyl is selected from $C_1$ to $C_6$ alkyl and $C_1$ to $C_6$ hydroxyalkyl.

More preferred $R^2$ include: $C_1$ to $C_6$ alkyl; $C_2$ to $C_6$ alkenyl; and $C_1$ to $C_6$ haloalkyl.

More preferred $R^4$ include: hydrogen; fluoro; cyano; and methyl.

Even more preferred X include: fluoro; chloro; bromo; nitro; cyano; methyl; ethyl; methoxymethyl; methoxy; methylthio; and acetyl.

Even more preferred $R^1$ include: hydrogen; benzoyl; acetyl; pivaloyl; and the alkali metal ions.

Even more preferred $R^2$ include: ethyl; 2-fluoroethyl; and allyl.

Even more preferred $R^3$ include ethyl and n-propyl.

Even more preferred $R^4$ include hydrogen.

Especially preferred X include: fluoro; chloro; nitro; and methyl.

Especially preferred $R^1$ include hydrogen and the alkali metal ions sodium and potassium.

Especially preferred $R^2$ include ethyl.

Especially preferred n include the integer 1.

Among the particularly preferred compounds of the invention are compounds of formula

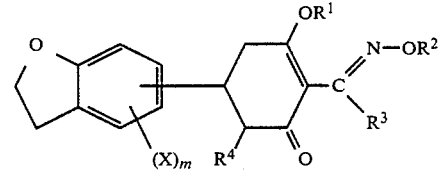

wherein:

X, which may be the same or different, are selected from chloro and methyl;

$R^1$ is selected from the group consisting of hydrogen and the alkali metal ions sodium and potassium;

$R^2$ is ethyl;

$R^3$ is selected from ethyl and n-propyl;

$R^4$ is hydrogen; and m is the integer 3.

Examples of compounds embraced by the invention include:

2-[1-(ethoxyimino)butyl]-5-(2,3-dihydro-4,5,6-trimethylbenzo[b]furan-7-yl)-3-hydroxycyclohex-2-en-1-one;

2-[1-(allyloxyimino)propyl]-5-(2,3-dihydro-4,5,6-trimethylbenzo[b]furan-7-yl)-3-hydroxycyclohex-2-en-1-one;

2-[1-(ethoxyimino)butyl]-4-fluoro-5-(2,3-dihydro-5,6,7-trimethylbenzo[b]furan-4-yl)-3-hydroxycyclohex-2-en-1-one;

5-(5-acetyl-2,3-dihydro-4,6-dimethylbenzo[b]furan-7-yl)-2-[1-(ethoxyimino)propyl]-3-hydroxycyclohex-2-en-1-one;

2-[1-(2-fluoroethoxyimino)butyl]-5-(2,3-dihydro-4,5-dimethyl-6-methoxybenzo[b]furan-7-yl)-3-hydroxycyclohex-2-en-1-one;

2-[1-(ethoxyimino)butyl]-5-(5,6,7-trimethylchroman-8-yl)-3-hydroxycyclohex-2-en-1-one;

2-[1-(ethoxyimino)propyl]-5-(2,3-dihydro-4,5,6-trimethylbenzo[b]thien-7-yl)-3-hydroxycyclohex-2-en-1-one;

2-[1-(ethoxyimino)propyl]-5-(2,3-dihydro-5,6,7-trimethyl-1,4-benzodithiin-8-yl)-3-hydroxycyclohex-2-en-1-one;

2-[1-(ethoxyimino)propyl]-5-(2,3-dihydro-4,6-dimethylbenzo[b]furan-7-yl)-3-hydroxycyclohex-2-en-1-one;

2-[1-(ethoxyimino)propyl]-5-(2,3-dihydro-7-methylbenzo[b]furan-4-yl)-3-hydroxycyclohex-2-en-1-one;

2-[1-(ethoxyimino)butyl]-5-(2,3-dihydro-4,5,6-trimethylbenzo[b]furan-7-yl)-3-hydroxy-4-methylcyclohex-2-en-1-one;

4-cyano-2-[1-(ethoxyimino)propyl]-5-(2,3-dihydro-5,6,7-trimethylbenzo[b]furan-4-yl)-3-hydroxycyclohex-2-en-1-one;

4-(ethoxycarbonyl)-2-[1-(ethoxyimino)butyl]-5-(2,3-dihydro-4,6-dimethylbenzo[b]furan-7-yl)-3-hydroxycyclohex-2-en-1-one;

and the lithium, potassium, sodium, copper, nickel and tetra(n-butyl)ammonium salts thereof;

3-benzoyloxy-2-[1-(ethoxyimino)butyl]-5-(2,3-dihydro-4,5,6-trimethylbenzo[b]furan-7-yl)cyclohex-2-en-1-one;

3-acetyloxy-2-[1-(ethoxyimino)butyl]-5-(2,3-dihydro-4,5,6-trimethylbenzo[b]furan-7-yl)cyclohex-2-en-1-one;

2-[1-(ethoxyimino)propyl]-5-(2,3-dihydro-4,5,6-trimethylbenzo[b]furan-7-yl)-3-tosyloxycyclohex-2-en-1-one;

2-[1-(ethoxyimino)butyl]-5-(2,3-dihydro-4,5,6-trimethylbenzo[b]furan-7-yl)-3-pivaloyloxycyclohex-2-en-1-one; and 2-[1-(ethoxyimino)butyl]-5-(2,3-dihydro-4,5,6-trimethylbenzo[b]thien-7-yl)-3-pivaloyloxycyclohex-2-en-1-one.

Specific examples of the compounds of the invention include those compounds detailed in Tables 1a and 1b below.

TABLE 1a

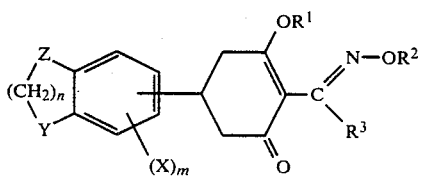

| Compound No | Z—(CH$_2$)$_n$—Y | (X)$_m$ | R$^1$ | R$^2$ | R$^3$ |
|---|---|---|---|---|---|
| 1 | 3,4-O—CH$_2$—O | all H | H | C$_2$H$_5$ | C$_2$H$_5$ |
| 2 | 3,4-O—CH$_2$—O | all H | Na | C$_2$H$_5$ | C$_2$H$_5$ |
| 3 | 4,5-O—CH$_2$—O | 2-NO$_2$ | H | C$_2$H$_5$ | C$_2$H$_5$ |
| 4 | 3,4-O—(CH$_2$)$_2$—O | all H | H | C$_2$H$_5$ | C$_2$H$_5$ |
| 5 | 2,3-O—CH$_2$—O | all H | H | C$_2$H$_5$ | CH$_2$CH$_2$CH$_3$ |

TABLE 1b

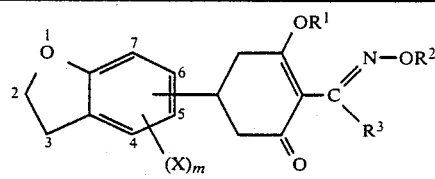

| Compound No | (X)$_m$ | Link | R$^1$ | R$^2$ | R$^3$ |
|---|---|---|---|---|---|
| 1 | 4,5,7-(CH$_3$)$_3$ | 6 | H | C$_2$H$_5$ | C$_2$H$_5$ |
| 7 | 4,6,7-(CH$_3$)$_3$ | 5 | H | C$_2$H$_5$ | C$_2$H$_5$ |
| 8 | 4,6,7-(CH$_3$)$_3$ | 5 | H | C$_2$H$_5$ | CH$_2$CH$_2$CH$_3$ |
| 9 | 4,5-(CH$_3$)$_2$—7-Cl | 6 | H | C$_2$H$_5$ | C$_2$H$_5$ |
| 10 | 5,6,7-(CH$_3$)$_3$ | 4 | H | C$_2$H$_5$ | CH$_2$CH$_2$CH$_3$ |
| 11 | 4,5,6-(CH$_3$)$_3$ | 7 | H | C$_2$H$_5$ | CH$_2$CH$_2$CH$_3$ |

The compounds of the invention may be prepared by a variety of methods and in a further aspect the invention provides methods for the preparation of compounds of formula I.

Conveniently the preparation of the compounds of the invention can be considered in three or four parts.

Part A involves the formation of a 5-(aryl)cyclohexane-1,3-dione of formula IX. This reaction may be carried out in a two step process by condensing an aldehyde derivative of formula V with acetone or an acetone derivative to form a ketone of formula VI, which is in turn condensed with a malonic acid ester derivative of formula VII to give a 5-(aryl)cyclohexane-1,3-dione of formula IX.

Scheme A(i)(a) is particularly suitable for the preparation of 5-(aryl)cyclohexane-1,3-dione derivatives of formula IX wherein R$^4$ is hydrogen, halogen or alkyl. The Scheme may also be used for the preparation of compounds of formula IX wherein R$^4$ is (C$_1$ to C$_6$ alkoxy)carbonyl by isolation of the intermediate of formula VIII as that intermediate of formula VIIIa wherein R$^4$ is hydrogen is the 5-(aryl)cyclohexane-1,3-dione of formula IX wherein R$^4$ is (C$_1$ to C$_6$ alkoxy)carbonyl.

Scheme A(i)(b) is particularly suitable for the preparation of 5-(aryl)cyclohexane-1,3-dione derivatives of formula IX wherein R$^4$ is alkyl.

Scheme A(i)(c) is particularly suitable for the preparation of 5-(aryl)cyclohexane-1,3-dione derivatives of formula IX wherein R$^4$ is cyano or (C$_1$ to C$_6$ alkoxy)carbonyl.

Alternatively, this preparation may be carried out in a two step process by condensing an aldehyde derivative of formula V with a malonic acid ester of formula VIIb to give an arylmethylidenemalonate derivative of formula X which is in turn condensed with an acetoacetic acid ester derivative of formula XI to give a 5-(aryl)cyclohexane-1,3-dione of formula IX, either with or without isolation of the intermediate of formula XII.

In a further alternative process this preparation may be carried out by condensing a 2-arylalkenoate derivative of formula XXI with an acetoacetic acid ester derivative of formula XI to give a 5-(aryl)cyclohexane-1,3-dione of formula IX, either with or without isolation of the intermediate of formula VIIIa.

The above reaction sequences are set out in SCHEME A parts (i), (ii) and (iii) respectively below, wherein R represents a C$_1$ to C$_6$ alkyl group.

SCHEME A

-continued
SCHEME A

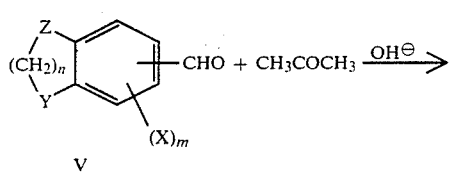
V (i)(a)

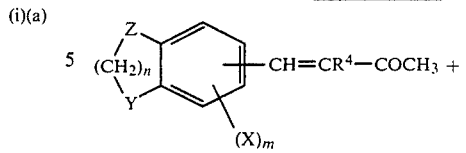
VIb

CH₂(CO₂R)₂ $\xrightarrow{(1)\ RO^\ominus}{(2)\ H^\oplus}$

VIIb

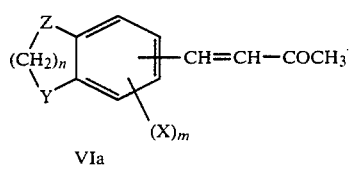
VIa

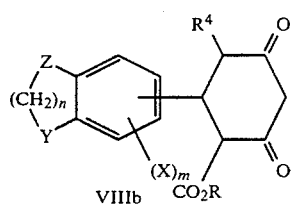
VIIIb

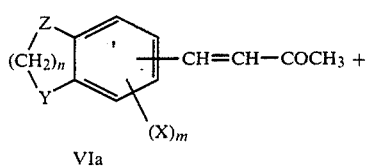
VIa +

R⁴CH(CO₂R)₂ $\xrightarrow{(1)\ RO^\ominus}{(2)\ H^\oplus}$

VIIa

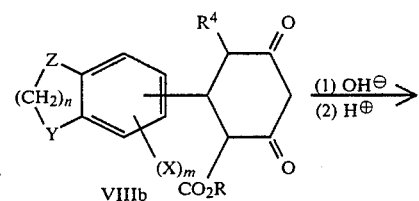
VIIIb  $\xrightarrow{(1)\ OH^\ominus}{(2)\ H^\oplus}$

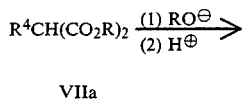
VIIIa

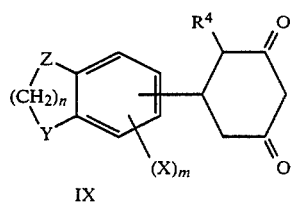
IX

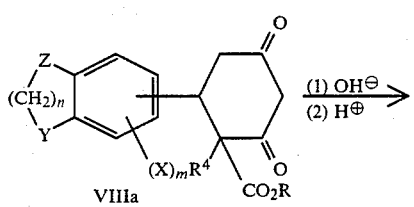
VIIIa $\xrightarrow{(1)\ OH^\ominus}{(2)\ H^\oplus}$ (i)(c)

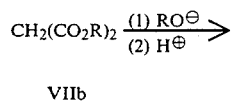
VIa +

R⁴CH₂CO₂R $\xrightarrow{(1)\ RO^\ominus}{(2)\ H^\oplus}$

VIIc

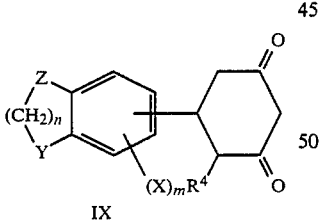
IX

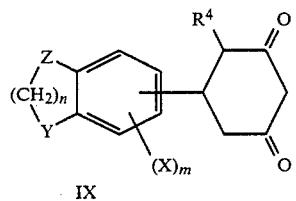
IX

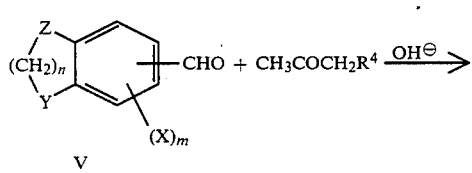
V + CH₃COCH₂R⁴ $\xrightarrow{OH^\ominus}$ (i)(b)

(ii)

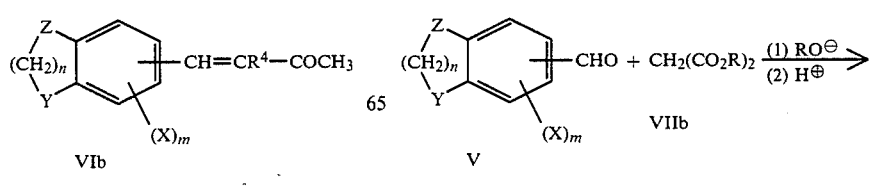
V + CH₂(CO₂R)₂ $\xrightarrow{(1)\ RO^\ominus}{(2)\ H^\oplus}$

VIIb

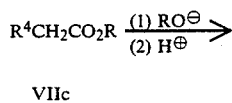
VIb

-continued
SCHEME A

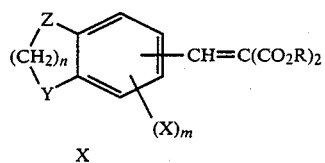
X

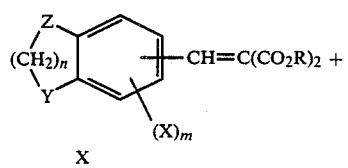
X

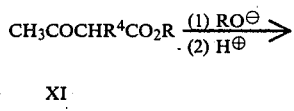
XI

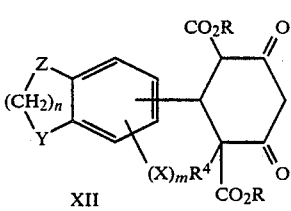
XII

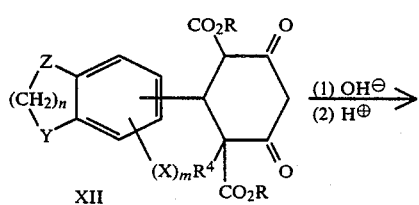
XII

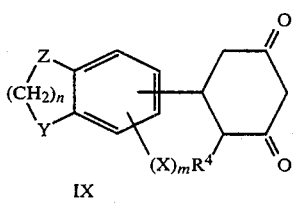
IX

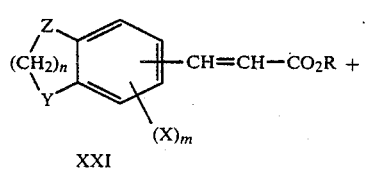
XXI

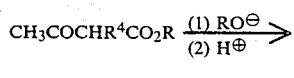
XI

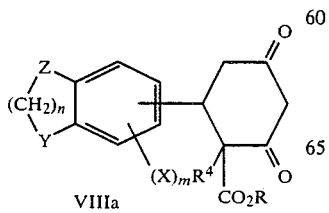
VIIIa

-continued
SCHEME A

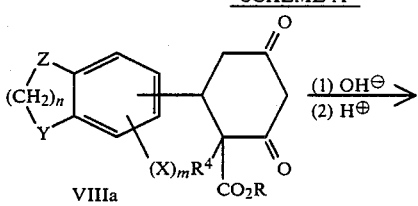
VIIIa

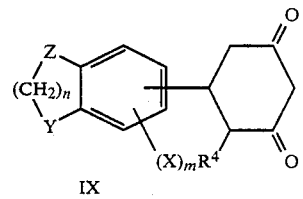
IX

Part B involves the acylation of a compound of formula IX to give a 2-acyl-5-(aryl)cyclohexane-1,3-dione of formula XIII. This reaction may be carried out by reacting a 5-(aryl)cyclohexane-1,3-dione of formula IX with:

(iv) a mixture of an acid anhydride of formula XIV and either a salt of that acid or an alkoxide salt wherein M is an alkali metal ion and R is $C_1$ to $C_6$ alkyl;

(v) a mixture of an acid anhydride of formula XIV and the corresponding acid;

(vi) an acid halide of formula XV;

(vii) a mixture of an acid halide of formula XV and the corresponding acid; or (viii) an alkali metal or alkaline earth metal hydride followed by reaction with an acid anhydride of formula XIV or an acid chloride of formula XV.

Alternatively this reaction may be carried out by:

(ix) reacting a 5-(aryl)cyclohexane-1,3-dione of formula IX with an acid halide of formula XV in the presence of pyridine to give an intermediate O-acyl derivative of formula XVI; and (x) reacting the intermediate of formula XVI with a Lewis acid catalyst;

(xi) reacting the intermediate of formula XVI with the corresponding acid of the acid halide of formula XV; or (xii) reacting the intermediate of formula XVI with imidazole.

Each of these reactions is outlined in SCHEME B below wherein hal represents halogen.

SCHEME B

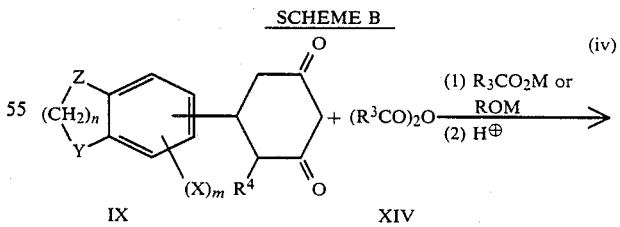
IX                                    XIV (iv)

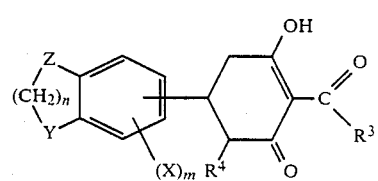
XIII

-continued
SCHEME B (v)
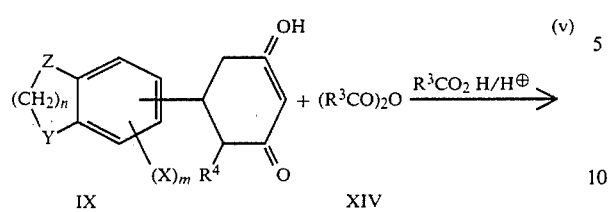 + $(R^3CO)_2O$ $\xrightarrow{R^3CO_2H/H^\oplus}$ 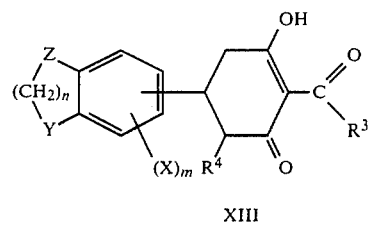

IX    XIV    XIII

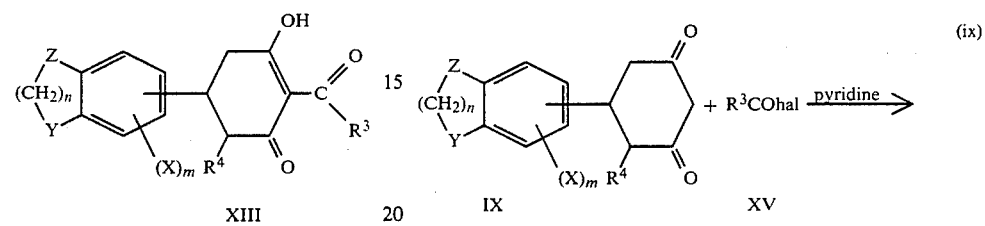

XIII (vi)
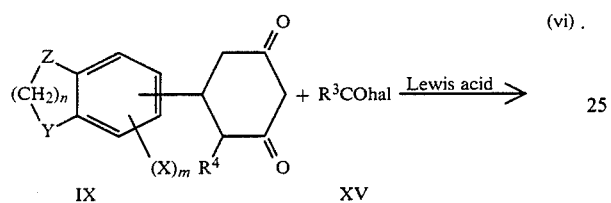 + $R^3COhal$ $\xrightarrow{\text{Lewis acid}}$ 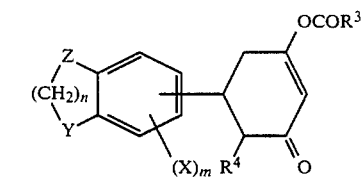

IX    XV

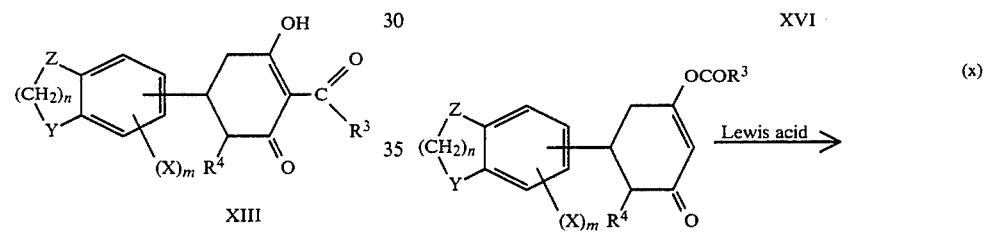

XIII (vii)
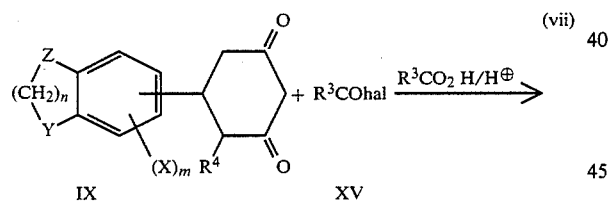 + $R^3COhal$ $\xrightarrow{R^3CO_2H/H^\oplus}$

IX    XV

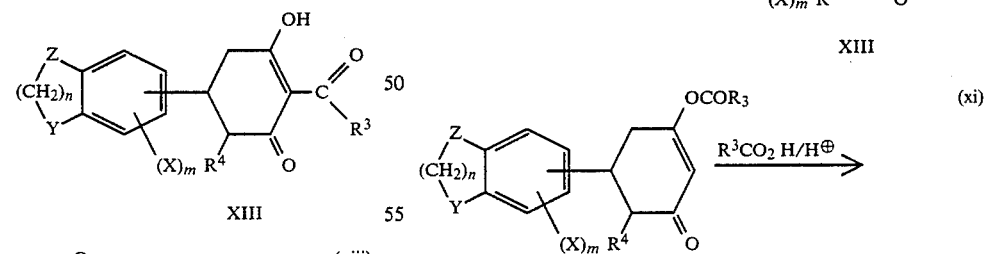

XIII (viii)
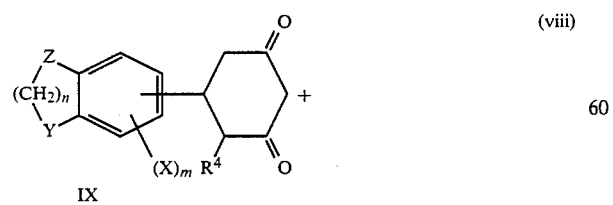 +

IX $(R^3CO)_2O$ or $R^3COhal$ $\xrightarrow[\text{(2) XIV or XV}]{\text{(1) }H^\ominus}$

XIV    XV (ix)
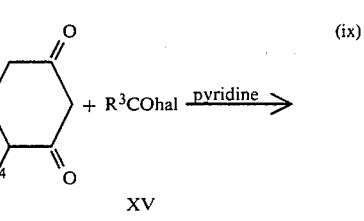 $\xrightarrow{\text{pyridine}}$

IX    XV

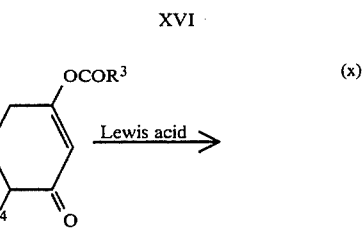

XVI (x)
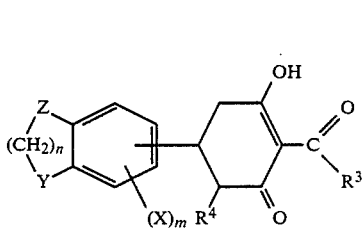 $\xrightarrow{\text{Lewis acid}}$

XVI

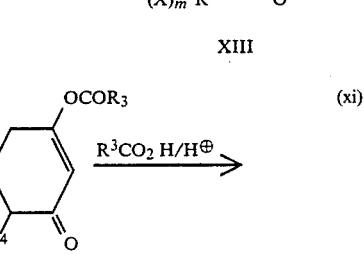

XIII (xi)
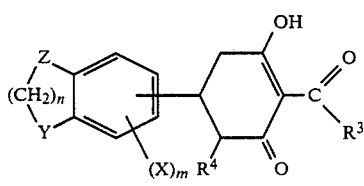 $\xrightarrow{R^3CO_2H/H^\oplus}$

XVI

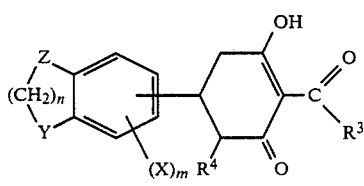

XIII

-continued
SCHEME B

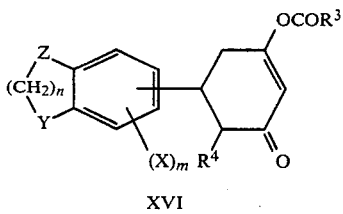

XVI

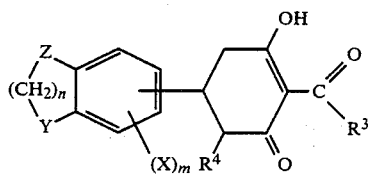

XIII

Part C involves the formation of a compound of the invention of formula I wherein R¹ is hydrogen, that is a compound of formula II. This reaction may be carried out either:

(xiii) by reacting a compound of formula XIII with an alkoxyamine derivative of formula XVII to give a compound of formula II; or (xiv) by reacting a compound of formula XIII with hydroxylamine to give an intermediate oxime derivative of formula XVIII and reacting the oxime derivative of formula XVIII with an alkylating agent of formula XIX to give a compound of formula II.

These reaction sequences are set out in SCHEME C below wherein L is a good leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

SCHEME C

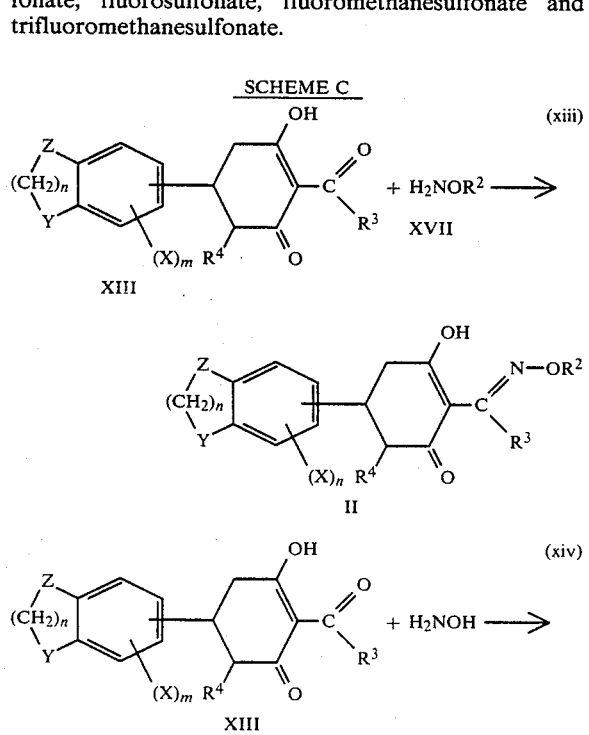

-continued
SCHEME C

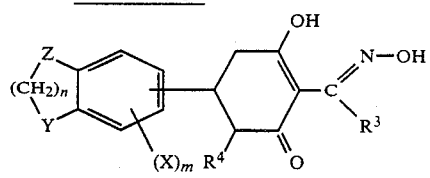

XVIII

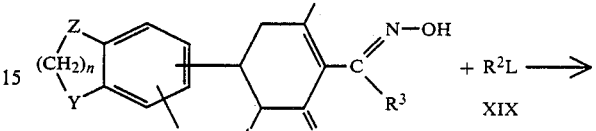

XVIII

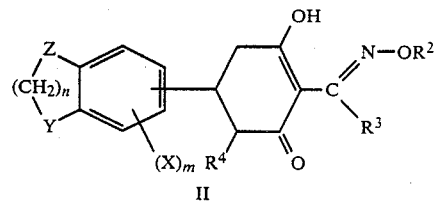

II

Compounds of the invention of formula I wherein R¹ is not hydrogen may be prepared from compounds of the invention of formula I wherein R¹ is hydrogen, that is, compounds of formula II, by etherification acylation or sulfonylation as required. This reaction is outlined in SCHEME D below.

SCHEME D

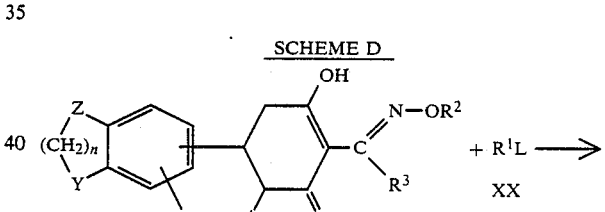

II

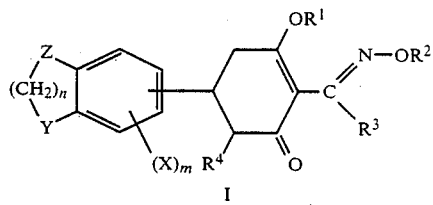

I

Compounds of the invention of formula I wherein R¹ is an inorganic or organic cation may be prepared from the compounds of the invention of formula I wherein R¹ is hydrogen, that is, compounds of formula II, by reacting said compounds of formula II with an inorganic or organic salt. For example, the compounds of formula I wherein R¹ is an alkali metal ion may be prepared by reacting the appropriate compound of formula II with the appropriate alkali metal hydroxide or alkoxylate. The compounds of formula I wherein R¹ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, wherein Z, Y, X, $R^1$, $R^2$, $R^3$, $R^4$, m and n are as hereinbefore defined, which process comprises:

(a) reacting an aldehyde derivative of formula V with acetone or an acetone derivative to give a ketone derivative of formula VI and reacting the ketone derivative of formula VI with a malonic acid ester derivative of formula VII, wherein R is $C_1$ to $C_6$ alkyl, to give a 5-(aryl)cyclohexane-1,3-dione derivative of formula IX; or reacting an aldehyde derivative of formula V with a malonic acid ester of formula VII to give an arylmethylidenemalonate derivative of formula X and reacting the arylmethylidenemalonate derivative of formula X with an acetoacetic acid ester derivative of formula XI, wherein R is $C_1$ to $C_6$ alkyl, to give a 5-(aryl)cyclohexane-1,3-dione derivative of formula IX; or reacting a 2-arylalkenoate derivative of formula XXI, wherein R is $C_1$ to $C_6$ alkyl, with an acetoacetic acid ester derivative of formula XI, wherein R is $C_1$ to $C_6$ alkyl, to give a 5-(aryl)cyclohexane-1,3-dione derivative of formula IX;

(b) acylating the 5-(aryl)cyclohexane-1,3-dione derivative of formula IX with an acid anhydride of formula XIV or an acid halide of formula XV to give a 2-acyl-5-(aryl)cyclohexane-1,3-dione derivative of formula XIII;

(c) reacting the 2-acyl-5-(aryl)-cyclohexane-1,3-dione derivative of formula XIII with an alkoxyamine derivative of formula XVII to give a compound of the invention of formula II or reacting the 2-acyl-5-(aryl)cyclohexane-1,3-dione derivative of formula XIII with hydroxylamine and alkylating the oxime intermediate of formula XVIII with an alkylating agent of formula XIX, wherein L is a good leaving group, to give a compound of the invention of formula II; and optionally (d) reacting the compound of the invention of formula II with a compound of formula XX, wherein L is a good leaving group, to give a compound of the invention of formula I.

Certain of the intermediate compounds of formulae VI, VIII, IX, X, XII, XXI, XIII, XVI and XVIII are novel compounds and therefore as a further embodiment the invention provides novel compounds of formulae VI, VIII, IX, X, XII, XXI, XIII, XVI and XVIII, wherein the substituents are as hereinbefore defined, and processes for the preparation thereof.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against monocotyledonous plants, or grasses. However, certain of the compounds of formula I are selectively active within the group of monocotyledonous plants and may be used at a rate sufficient to kill or severely damage monocotyledonous weeds in a monocotyledonous cereal crop.

Therefore, in yet a further aspect the invention provides a process for selectively controlling the growth of weeds in crops which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant postemergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an inert carrier therefor.

Certain of the compounds of formula I exhibit useful plant growth regulating activity. For example, while certain compounds of formula I show selective herbicidal activity against wild grasses in crops of cultivated plants, at some rates of application they exhibit plant growth regulating effects in said crops.

Plant growth regulating effects may be manifested in a number of ways. For example, suppression of apical dominance, stimulation of auxiliary bud growth, stimulation of early flowering and increase in seed formation, enhancement of flowering and increase in seed yield, stem thickening, stem shortening and tillering. Plant growth regulating effects shown by compounds of the invention include, for example, tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the type of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meal and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal, and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acid, the di- and tri-isopropylnaphthalenesulfonic acids, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsuflate and the mono esters of sulfuric acid with fatty alcohol glycol ethers. Nonionic surface active agents include: the condensation products of ethylene oxide with fatty alcohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersion of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 20 to 99%, preferably 20 to 60%, by weight of active ingredient.

Emulsion or emulsifiable concentrates are conveniently prepared by dissolving the active ingredient in an organic solvent containing one or more surface active agents. Pastes may be prepared by blending the finely divided active ingredient with a finely divided solid carrier, one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active ingredient, water, at least one surface active agent and preferably at least one suspending agent. Suitable suspending agents include: hydrophilic colloids such as, for example, poly(N-vinylpyrrolidone), sodium carboxymethylcellulose and the vegetable gums gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts, either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl(3-methylphenyl)-carbamate (common name phenmedipham) and 3-[(ethoxycarbonyl)amino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name aziproptryne);

K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiocarbamate herbicides such as S-propyl dipropylthiocarbamate (common name verolate);

M. 1,2,4-triazin-5-one herbicides such as 4-amino-4,5-dihydro-3-methyl-6-phenyl-1,2,4-triazine-5-one (common name metamitron) and 4-amino-6-tert-butyl-4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

O. anilide herbicides such as N-butoxymethyl-α-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189); and T. miscellaneous herbicides including N,N-dimethyldiphenylacetamide (common name diphenamid), N-(1- naphthyl)phthalamic acid (common name naptalam) and 3-amino-1,2,4-triazole.

Examples of useful contact herbicides include:
U. bipyridylium herbicides such as those in which the active entity is the 1,1'-dimethyl-4,4'-dipyridylium ion (common name paraquat) and those in which the active entity is the 1,1'-ethylene 2,2'-dipyridylium ion (common name diquat);
V. organoarsenical herbicides such as monosodium methanearsonate (common name MSMA); and
W. amino acid herbicides such as N-(phosphonomethyl)glycine (common name glyphosate) and its salts and esters.

The invention is now illustrated by, but in no way limited to, the following examples.

EXAMPLE 1

2-[1-(Ethoxyimino)propyl]-3-hydroxy-5-(3,4-methylenedioxyphenyl)cyclohex-2-en-1-one (1)

(i) An aqueous solution of 10% sodium hydroxide (3.5 ml) was added dropwise to a solution of piperonal (20.0 g) in acetone (27 ml) and water (14 ml), the temperature of the reaction mixture being maintained below 30° C. during the addition. On completion of the reaction (ca 2 hr) the reaction mixture was poured into water and the precipitate was filtered off and dried to give 1-(3,4-methylenedioxyphenyl)but-1-en-3-one as a crystalline solid, mp 108° C. (from ethanol).

(ii) Diethyl malonate (17.34 g) was added to a solution of sodium metal (2.35 g) in anhydrous absolute ethanol (40 ml). 1-(3,4-methylenedioxyphenyl)-but-1-en-3-one (20 g) was added to the solution and the volume of ethanol was made up to 80 ml. The mixture was heated under reflux with stirring for 2-4 hr. An aqueous solution of potassium hydroxide (25.0 g in 120 ml of water) was added and the mixture was heated under reflux for a further 6 hours. Subsequently, the ethanol was distilled off and the aqueous residue was acidified with dilute hydrochloric acid. After cooling to room temperature, the mixture was extracted with ethyl acetate and the organic phase was washed consecutively with water and an aqueous 10% sodium hydroxide solution. The basic extract was acidified with dilute aqueous hydrochloric acid and the resulting solution was extracted with ethyl acetate. The organic phase was washed with water, dried over anhydrous sodium sulfate, and the solvent was evaporated to give 3-hydroxy-5-(3,4-methylenedioxyphenyl)cyclohex-2-en-1-one as a crystalline solid, mp 181° C.

(iii) Propionic anhydride (30 ml) was added cautiously to freshly prepared sodium methoxide (0.3 g). On completion of the reaction 3-hydroxy-5-(3,4-methylenedioxyphenyl)cyclohex-2-en-1-one (5.0 g) was added and the reaction mixture was heated at 160° C. for a period of 75 minutes. The excess propionic anhydride was removed by distillation under reduced pressure. Aqueous 3M potassium hydroxide was added to the residue and the mixture was heated under reflux for a period of 3 hours. The reaction mixture was cooled, poured into water (100 ml) and acidified with dilute hydrochloric acid. The aqueous mixture was extracted with diethyl ether, the organic phase was washed with water, dried over anhydrous sodium sulfate, and the solvent was evaporated. The residue was purified by column chromatography over silica gel (eluant dichloromethane) to give 3-hydroxy-5-(3,4-methylenedioxyphenyl)-2-propionylcyclohex-2-en-1-one as a crystalline solid, mp 129° C.

(iv) A solution of sodium hydroxide (0.15 g) in water and then ethoxyamine hydrochloride (0.37 g) were added to a solution of 3-hydroxy-5-(3,4-methylenedioxyphenyl)-2-propionylcyclohex-2-en-1-one (1.0 g) in ethanol (40 ml) The mixture was stirred at room temperature and the progress of the reaction was monitored by thin layer chromatography (eluant dichloromethane). On completion of the reaction the solvent was removed by distillation under reduced pressure. The residue was dissolved in dichloromethane and the organic phase was washed with water and dried over anhydrous sodium sulphate. The solvent was evaporated to give 2-[1-(ethoxyimino)propyl]-3-hydroxy-5-(3,4-methylenedioxyphenyl)cyclohex-2-en-1-one as an oil.

The product was characterized by proton nuclear magnetic resonance spectroscopy. Pmr spectrum (CDCl$_3$; $\delta$in ppm): 1.08–1.38 (6H, 2xt), 2.59–3.07 (7H, m); 4.10 (2H, q); 5.89 (2H, s); 6.70 (3H, s); 14.76 (1H, brs).

EXAMPLE 2

Sodium salt of 2-[1-(ethoxyimino)propyl]-3-hydroxy-5-(3,4-methylenedioxyphenyl)cyclohex-2-en-1-one (2)

A solution of sodium hydroxide (0.024 g) in water (1 ml) was added to a solution of 2-[1-(ethoxyimino)propyl]-3-hydroxy-5-(3,4-methylenedioxyphenyl)cyclohex-2-en-1-one (0.20 g) in toluene (30 ml). The solvent was removed by distillation under reduced pressure to yield the title compound as a yellow solid, mp>150° C. (dec.).

EXAMPLE 3

2-[1-(Ethoxyimino)propyl]-3-hydroxy-5-(2-nitro-4,5-methylenedioxyphenyl)cyclohex-2-en-1-one (3)

(i) A solution consisting of fuming nitric acid (0.84 g), glacial acetic acid (0.54 g) and acetic anhydride (0.54 g) was added to a mixture of 3-hydroxy-5-(3,4-methylenedioxyphenyl)-2-propionylcyclohex-2-en-1-one (2.60 g) and acetic anhydride (1.62 g) at 0° C. The mixture was stirred at 0°–3° C. for 1.5 hours with addition of extra portions of acetic anhydride when necessary to aid the stirring. The mixture was poured into water and the precipitate was collected and dried giving 3-hydroxy-5-(2-nitro-4,5-methylenedioxyphenyl)-2-propionylcyclohex-2-en-1-one as a yellow solid, mp 139° C.

(ii) 2-[1-(Ethoxyimino)propyl]-3-hydroxy-5-(2-nitro-4,5-methylenedioxyphenyl)cyclohex-2-en-1-one was prepared from 3-hydroxy-5-(2-nitro-4,5-methylenedioxyphenyl)-2-propionylcyclohex-2-en-1-one following essentially the same procedure as that described in Example 1 part (iv). The product was obtained as a yellow solid, mp 122° C. and was characterized by proton nuclear magnetic resonance spectroscopy. Pmr spectrum (CDCl$_3$; $\delta$ in ppm): 1.07–1.38 (6H,m); 2.48–3.11 (6H,m); 3.80–4.27 (3H,m); 6.14 (2H,s); 6.89 (1H,s); 7.38 (1H,s); 15.22 (1H,brs).

EXAMPLE 4

2-[1-(Ethoxyimino)propyl]-3-hydroxy-5-(3,4-ethylenedioxyphenyl)cyclohex-2-en-1-one (4)

(i)(a) A mixture of 3,4-dihydroxybenzaldehyde (10.0 g), ethylene dibromide (13.61 g), copper powder (trace), sodium hydroxide (5.80 g) and ethanol (500 ml)

was heated at reflux for 2 days. Subsequently, the solvent was evaporated and the residue was dissolved in dichloromethane. The organic phase was shaken with a little water and then dried over anhydrous magnesium sulphate. The solvent was evaporated and the residue was purified by column chromatography over silica gel (eluant dichloromethane) giving 3,4-ethylenedioxybenzaldehyde as an oil. The product was characterized by proton nuclear magnetic resonance spectroscopy. Pmr spectrum (CDCl$_3$; δ in ppm): 4.35 (4H, s); 6.98 (1H, d); 7.40 (2H, m); 9.70 (1H, s).

(i)(b) 1-(3,4-Ethylenedioxyphenyl)but-1-en-3-one was prepared from 3,4-ethylenedioxybenzaldehyde and acetone following essentially the same procedure as that described in Example 1 part (i). The product was obtained as a crystalline solid, mp 80° C.

(ii) 5-(3,4-Ethylenedioxyphenyl)-3-hydroxycyclohex-2-en-1-one was prepared from 1-(3,4-ethylenedioxyphenyl)but-1-en-3-one and diethyl malonate following essentially the same procedure as that described in Example 1 part (ii). The product was obtained as a crystalline solid, mp 188° C.

(iii) 5-(3,4-Ethylenedioxyphenyl)-3-hydroxy-2-propionylcyclohex-2-en-1-one was prepared from 5-(3,4-ethylenedioxyphenyl)-3-hydroxycyclohex-2-en-1-one and propionic anhydride following essentially the same procedure as that described in Example 1 part (iii). The product was obtained as a crystalline solid, mp 155° C.

(iv) 2-[1-(Ethoxyimino)propyl]-5-(3,4-ethylenedioxyphenyl)-3-hydroxycyclohex-2-en-1-one was prepared from 5-(3,4-ethylenedioxyphenyl)-3-hydroxy-2-propionylcyclohex-2-en-1-one and ethoxyamine hydrochloride following essentially the same procedure as that described in Example 1 part (iv). The product was obtained as an oil and was characterized by proton nuclear magnetic resonance spectroscopy. Pmr spectrum (CDCl$_3$; δ in ppm): 1.08–1.40 (6H, 2xt); 2.27–3.25 (7H, m); 4.00–4.24 (6H, m); 6.65–7.27 (3H, m); 15.00 (1H, brs).

EXAMPLE 5

2-[1-(Ethoxyimino)butyl]-3-hydroxy-5-(2,3-methylenedioxyphenyl)cyclohex-2-en-1-one (5)

(i) (a) A mixture of 2,3-dihydroxybenzaldehyde (6.4 g, 50 mmol) and sodium hydroxide (5 g in 25 ml of water) was added over 110 mins to a refluxing mixture of methylene bromide (17.3 g, 100 mmol), N,N,N-[tri-(C$_8$ to C$_{10}$ alkyl)]-N-methylammonium chloride (0.5 g; supplied by Aldrich Chemicals under the Trade Name "Adogen" 464) and water (10 ml). The mixture was heated at reflux for a further 5 hr under nitrogen and then steam distilled. The distillate was extracted with dichloromethane. Evaporation of the dried (MgSO$_4$) organic extract gave 2,3-methylenedioxybenzaldehyde (3.2 g, 46%) as a yellow oil. Pmr spectrum (CDCl$_3$; δ in ppm): 6.03 (2H,s); 6.66–6.99 (2H,m); 7.02–7.25 (1H,m); 9.97 (1H,s).

(b) 1-(2,3-Methylenedioxyphenyl)but-1-en-3-one was prepared from 2,3-methylenedioxybenzaldehyde following essentially the same procedure as that described in Example 1 part (i) and was obtained as a yellow oil. Pmr spectrum (CDCl$_3$; δ in ppm): 2.32 (3H,s); 5.99 (2H,s); 6.61–7.03 (4H,m); 7.37 (1H,d).

(ii) and (iii) Sodium metal (0.86 g, 37 mmol) was dissolved in dry absolute ethanol (30 ml) and diethyl malonate (6 g, 37 mmol) was added. The mixture was heated to reflux and 1-(2,3-methylenedioxyphenyl)but-1-en-3-one (3.37 g, 19 mmol) dissolved in dry absolute ethanol (15 ml) was added. After 4 hr, the solvent was removed by reduced pressure distillation and the solid residue was thoroughly dried. Dry dimethylformamide (40 ml) was added and the mixture was heated to 120° C. under nitrogen. n-Butyric anhydride (6.01 g, 39 mmol) was added and the mixture was heated at reflux for 4 hr. After cooling, the mixture was extracted with ether. The aqueous layer was heated to 60° C. and was acidified (to pH 5) by dropwise addition of a dilute hydrochloric acid solution. After cooling, the mixture was extracted with dichloromethane. The residue obtained after evaporation of the dried (MgSO$_4$) organic extract was purified by column chromatography over silica gel with dichloromethane elution to give 2-butyryl-3-hydroxy-5-(2,3-methylenedioxyphenyl)cyclohex-2-en-1-one as a pale yellow solid, mp 81°–82° C.

(iv) 2-[1-(Ethoxyimino)butyl]-3-hydroxy-5-(2,3-methylenedioxyphenyl)cyclohex-2-en-1-one was prepared from 2-butyryl-3-hydroxy-5-(2,3-methylenedioxyphenyl)cyclohex-2-en-1-one following essentially the same procedure as that described in Example 1 part (iv), and was obtained as a colourless oil. The product was characterized by proton nuclear magnetic resonance spectroscopy. Pmr spectrum (CDCl$_3$; δ in ppm): 0.98 (3H,t); 1.31 (3H,t); 1.58 (2H,m); 2.49–3.11 (6H,m); 3.11–3.62 (1H,m); 4.07 (2H,q); 5.88 (2H,s); 6.44–6.87 (3H,m); 15.04 (1H,broad s).

EXAMPLE 6

5-(2,3-Dihydro-4,5,6-trimethylbenzo[b]furan-7-yl-2-[1-(ethoxyimino)butyl]-3-hydroxycyclohex-2-en-1-one (11)

(i) (a) A 40% aqueous formaldehyde solution (16.3 ml, 218 mmol) was added dropwise to a mixture of 3,4,5-trimethylphenol (29.6 g, 218 mmol) and a 26% aqueous dimethylamine solution (38 ml). The mixture was allowed to stand at room temperature overnight and was then poured into a dilute hydrochloric acid solution (15%, 200 ml). The mixture was extracted with ether and the aqueous acidic fraction was carefully neutralized with a 20% sodium hydroxide solution. The dried (Na$_2$SO$_4$) ether extract was evaporated to give 2-(dimethylaminoethyl)-3,4,5-trimethylphenol (31.9 g, 76%) as a white solid, mp 72° C.

(b) A mixture of 2-(dimethylaminomethyl)-3,4,5-trimethylphenol (31.85 g, 165 mmol) and iodomethane (31 ml, 495 mmol) in dichloromethane (250 ml) was allowed to stand at room temperature for 72 hours. The methiodide was filtered off and used without further purification.

(c) A solution of dimethylsulfoxonium methylide was prepared by adding trimethylsulfoxonium iodide (36.3 g, 165 mmol) to a well-stirred mixture of sodium hydride (165 mmol) and anhydrous dimethylsulfoxide (200 ml) at room temperature under nitrogen. 2-(Dimethylaminomethyl)-3,4,5-trimethylphenol methiodide (165 mmol) was added and the mixture was stirred at room temperature for 24 hr. The mixture was poured onto an ice-water mixture which was then extracted with dichloromethane. Evaporation of the dried (Na$_2$SO$_4$) organic extract followed by column chromatography of the residue over silica with dichloromethane elution gave 2,3-dihydro-4,5,6-trimethylbenzo[b]furan (7.84 g, 29%) as a pale yellow oil.

(d) 2,3-Dihydro-4,5,6-trimethylbenzo[b]furan-7-carboxaldehyde was prepared from 2,3-dihydro-4,5,6-trimethylbenzo[b]furan following the general method of Organic Synthesis, Coll. vol. v, 49 and was obtained as a yellow solid, mp 90° C.

(e) 1-(2,3-Dihydro-4,5,6-trimethylbenzo[b]furan-7-yl)but-1-en-3-one was prepared from 2,3-dihydro-4,5,6-trimethylbenzo[b]furan-7-carboxaldehyde and acetone following essentially the same procedure as that described in Example 1 part (i), and was obtained as a pale brown solid, mp 116° C.

(ii) 5-(2,3-Dihydro-4,5,6-trimethylbenzo[b]furan-7-yl)-3-hydroxycyclohex-2-en-1-one was prepared from 1-(2,3-dihydro-4,5,6-trimethylbenzo[b]furan-7-yl)but-1-en-3-one following essentially the same procedure as that described in Example 1 part (ii), and was obtained as a cream solid, mp 264° C.

(iii) 5-(2,3-Dihydro-4,5,6-trimethylbenzo[b]furan-7-yl)-3-hydroxycyclohex-2-en-1-one (1.5 g, 6 mmol) was added to a mixture of sodium hydride (6.6 mmol) and anhydrous dimethylformamide (50 ml) under nitrogen. After 15 min n-butyric anhydride (0.96 g, 6.6 mmol) was added and the mixture was heated and stirred at 110° C. for 2 hrs. After cooling, the mixture was poured into water (300 ml) which was then extracted with diethyl ether. The residue obtained after evaporation of the dried ($Na_2SO_4$) organic extract was purified by column chromatography over silica gel with dichloromethane elution to give 2-butyryl-5-(2,3-dihydro-4,5,6-trimethylbenzo[b]furan-7-yl)-3-hydroxycyclohex-2-en-1-one (0.96 g, 51%) as a pale yellow solid, mp 140° C.

(iv) 5-(2,3-Dihydro-4,5,6-trimethylbenzo[b]furan-7-yl)-2-[1-(ethoxyimino)butyl]-3-hydroxycyclohex-2-en-1-one was prepared from 2-butyryl-5-(2,3-dihydro-4,5,6-trimethylbenzo[b]furan-7-yl)-3-hydroxycyclohex-2-en-1-one following essentially the same procedure as that described in Example 1 part (iv), and was obtained as a white solid, mp 108° C. The product was characterized by proton nuclear magnetic resonance spectroscopy. Pmr spectrum ($CDCl_3$; δ in ppm): 0.99 (3H,t); 1.31 (3H,t); 1.56 (2H,m); 2.14 (3H,s); 2.18 (3H, s); 2.22 (3H,s); 2.22–3.18 (9H,m); 4.10 (2H,q); 4.51 (2H,t); 14.99 (1H,broad s).

EXAMPLE 7

2-[1-(Ethoxyimino)propyl]-5-(2,3-dihydro-4,5,7-trimethylbenzo[b]furan-6-yl)-3-hydroxycyclohex-2-en-1-one (6) was prepared from 2,4,5-trimethylphenol following essentially the same procedure as that described in Example 6.

(i) 2,3-Dihydro-4,5,7-trimethylbenzo[b]furan-6-carboxaldehyde was obtained as a yellow solid mp 93° C.

(ii) 5-(2,3-Dihydro-4,5,7-trimethylbenzo[b]furan-6-yl)-3-hydroxycyclohex-2-en-1-one was obtained as a cream solid. Proton magnetic resonance spectrum (DMSO-$d_6$; δ in ppm): 2.18 (3H,s); 2.19 (3H,s); 2.24 (3H,s); 2.26–3.32 (7H,m); 4.50 (2H,t); 5.39 (1H,s); 11.0 (1H,broad s).

(iii) 5-(2,3-Dihydro-4,5,7-trimethylbenzo[b]furan-6-yl)-3-hydroxy-2-propionylcyclohex-2-en-1-one was obtained as an oil. Proton magnetic resonance spectrum ($CDCl_3$; δ in ppm): 1.10 (3H, t); 2.18 (3H,s); 2.19 (3H,s); 2.21 (3H,s); 2.21–3.40 (9H,m); 4.50 (2H,t); 18.30 (1H,s).

(iv) 2-[1-(Ethoxyimino)propyl]-5-(2,3-dihydro-4,5,7-trimethylbenzo[b]furan-6-yl)-3-hydroxycyclohex-2-en-1-one was obtained as an oil. Proton magnetic resonance spectrum ($CDCl_3$; δ in ppm): 1.11–1.41 (6H,m); 2.16 (3H,s); 2.24 (6H,s); 2.24–3.25 (8H,m); 3.80 (1H,m); 4.12 (2H,q); 4.53 (2H, t); 12.60 (1H,broad s).

EXAMPLE 8

2-[1-(Ethoxyimino)propyl]-5-(2,3-dihydro-4,6,7-trimethylbenzo[b]furan-5-yl)-3-hydroxycyclohex-2-en-1-one (7) was prepared from 2,3,5-trimethylphenol following essentially the same procedure as that described in Example 6.

(i) 2,3-Dihydro-4,6,7-trimethylbenzo[b]furan-5-carboxaldehyde was obtained as a cream solid mp 99° C.

(ii) 5-(2,3-Dihydro-4,6,7-trimethylbenzo[b]furan-5-yl)-3-hydroxycyclohex-2-en-1-one was obtained as a cream solid mp 230° C.

(iii) 5-(2,3-Dihydro-4,6,7-trimethylbenzo[b]furan-5-yl-3-hydroxy-2-propionylcyclohex-2-en-1-one was obtained as an oil. Proton magnetic resonance spectrum ($CDCl_3$; δ in ppm): 1.18 (3H,t); 2.10 (3H,s); 2.20 (6H,s); 2.20–3.30 (8H,m); 3.80 (1H, m); 4.60 (2H,t); 18.10 (1H,s).

(iv) 2-[1-(Ethoxyimino)propyl]-5-(2,3-dihydro-4,6,7-trimethylbenzo[b]furan-5-yl)-3-hydroxycyclohex-2-en-1-one was obtained as a yellow oil. Proton magnetic resonance spectrum ($CDCl_3$; δ in ppm): 1.12–1.41 (6H,m); 2.12 (3H,s); 2.27 (6H,s); 2.27–3.22 (8H,m); 3.95–4.24 (3H,m); 4.53 (2H,t); 14.97 (1H,broad s).

EXAMPLE 9

2-[1-(Ethoxyimino)butyl]-5-(2,3-dihydro-4,6,7-trimethylbenzo[b]furan-5-yl)-3-hydroxycyclohex-2-en-1-one (8) was prepared from 5-(2,3-dihydro-4,6,7-trimethylbenzo[b]furan-5-yl)-3-hydroxycyclohex-2-en-1-one (see Example 8) following essentially the same procedure as that described in Example 6 parts (iii) and (iv).

(iii) 2-Butyryl-5-(2,3-dihydro-4,6,7-trimethylbenzo[b]furan-5-yl)-3-hydroxycyclohex-2-en-1-one was obtained as an oil. Proton magnetic resonance spectrum ($CDCl_3$; δ in ppm): 1.00 (3H, t); 1.70 (2H,m); 2.10 (3H,s); 2.20 (6H,s); 2.20–3.30 (8H, m); 3.80 (1H,m); 4.60 (2H,t); 18.10 (1H,s).

(iv) 2-[1-(Ethoxyimino)butyl]-5-(2,3-dihydro-4,6,7-trimethylbenzo[b]furan-5-yl)-3-hydroxycyclohex-2-en-1-one was obtained as a yellow oil. Proton magnetic resonance spectrum ($CDCl_3$; δ in ppm): 1.00 (3H,t); 1.32 (3H,t); 1.58 (2H,m); 2.12 (3H, s); 2.27 (6H,s); 2.27–3.22 (8H,m); 3.85 (1H,m); 4.11 (2H,q); 4.53 (2H,t); 15.08 (1H,broad s).

EXAMPLE 10

5-(7-Chloro-2,3-dihydro-4,5-dimethylbenzo[b]furan-6-yl)-2-[1-(ethoxyimino)propyl]-3-hydroxycyclohex-2-en-1-one (9) was prepared from 2-chloro-4,5-dimethylphenol following essentially the same procedure as that described in Example 6.

(i) 7-Chloro-2,3-dihydro-4,5-dimethylbenzo[b]furan-6-carboxaldehyde was obtained as a pale yellow solid, mp 129° C.

(ii) 5-(7-Chloro-2,3-dihydro-4,5-dimethylbenzo[b]furan-6-yl)-3-hydroxycyclohex-2-en-1-one was obtained as a tan solid, mp 224° C.

(iii) 5-(7-Chloro-2,3-dihydro-4,5-dimethylbenzo[b]furan-6-yl)-3-hydroxy-2-propionylcyclohex-2-en-1-one was obtained as an oil. Proton magnetic resonance spectrum ($CDCl_3$; δ in ppm): 1.18 (3H, t); 2.18 (6H,s); 2.50 (2H,t); 3.00–3.30 (4H,m); 4.60 (2H,t); 18.20 (1H,s).

(iv) 5-(7-Chloro-2,3-dihydro-4,5-dimethylbenzo[b]furan-6-yl)-2-[1-(ethoxyimino)propyl]-3-hydroxycyclohex-2-en-1-one was obtained as an oil. Proton magnetic resonance spectrum ($CDCl_3$; δ in ppm): 1.18–1.41 (6H,m); 2.18 (3H,s); 2.24 (3H, s); 2.24–2.55 (2H,m);

2.83–3.25 (4H,m); 3.25–4.17 (5H,m); 4.63 (2H,t); 15.02 (1H,broad s).

EXAMPLE 11

5-(2,3-Dihydro-5,6,7-trimethylbenzo[b]furan-4-yl)-2-[1-(ethoxyimino)butyl]-3-hydroxycyclohex-2-en-1-one (10)

(i) (a) 2,3-Dihydro-6,7-dimethylbenzo[b]furan-5-carboxaldehyde was prepared from 2,3-dimethylphenol following essentially the same procedure as that described in Example 6 part (i) (a) to (d), and was obtained as a pale yellow solid, mp 60° C. Pmr spectrum (CDCl$_3$; δ in ppm): 2.20 (3H,s); 2.50 (3H,s); 3.20 (2H,t); 4.60 (2H,t); 7.75 (1H,s); 10.05 (1H,s).

(b) Zinc amalgum [prepared by heating a mixture of zinc dust (7.0 g), mercuric chloride (0.70 g), concentrated hydrochloric acid (0.5 ml) and water (30 ml) for 5 minutes and then decanting the aqueous solution] was added to a mixture of 2,3-dihydro-6,7-dimethylbenzo[b]furan-5-carboxaldehyde (6.93 g, 39 mmol), acetic acid (50 ml), water (50 ml), and concentrated hydrochloric acid (100 ml). The mixture was heated at reflux with vigorous stirring for 12 hours. After cooling, the mixture was poured into water. The dried (Na$_2$SO$_4$) ether extract was evaporated and the residue was purified by column chromatography over silica with hexane elution to give 2,3-dihydro-5,6,7-trimethylbenzo[b]furan (5.00 g, 78%) as a white solid, mp <50° C.

(c) 2,3-Dihydro-5,6,7-trimethylbenzo[b]furan-4-carboxaldehyde was prepared from 2,3-dihydro-5,6,7-trimethylbenzo[b]furan following the general method of Organic Syntheses, Coll. Vol. V, 49 and was obtained as a low melting-point solid.

(d) 1-(2,3-Dihydro-5,6,7-trimethylbenzo[b]furan-4-yl)but-1-en-3-one was prepared from 2,3-dihydro-5,6,7-trimethylbenzo[b]furan-4-carboxaldehyde and acetone following essentially the same procedure as that described in Example 1 part (i), and was obtained as a brown oil.

(ii) 5-(2,3-Dihydro-5,6,7-trimethylbenzo[b]furan-4-yl)-3-hydroxycyclohex-2-en-1-one was prepared from 1-(2,3-dihydro-5,6,7-trimethylbenzo[b]furan-4-yl)but-1-en-3-one following essentially the same procedure as that described in Example 1 part (ii), and was obtained as a cream solid. Pmr spectrum (DMSO-d$_6$; δ in ppm): 2.15 (3H,s); 2.17 (3H,s); 2.22 (3H,s); 2.26–3.30 (7H,m); 4.49 (2H,t); 5.40 (1H,s); 11.0 (1H,broad s).

(iii) 2-Butyryl-5-(2,3-dihydro-5,6,7-trimethylbenzo[b]furan-4-yl)-3-hydroxycyclohex-2-en-1-one was prepared from 5-(2,3-dihydro-5,6,7-trimethylbenzo[b]furan-4-yl)-3-hydroxycyclohex-2-en-1-one following essentially the same procedure as that described in Example 6 part (iii), and was obtained as a yellow oil. Pmr spectrum (CDCl$_3$; δ in ppm): 1.00 (3H,t); 1.60 (2H,m); 2.15 (3H,s); 2.17 (3H,s); 2.22 (3H,s); 2.26–3.38 (8H,m); 3.74 (1H,m); 4.49 (2H,t); 15.20 (1H,broad s).

(iv) 5-(2,3-Dihydro-5,6,7-trimethylbenzo[b]furan-4-yl)-2-[1-(ethoxyimino)butyl]-3-hydroxycyclohex-2-en-1-one was prepared from 2-butyryl-5-(2,3-dihydro-5,6,7-trimethylbenzo[b]furan-4-yl)-3-hydroxycyclohex-2-en-1-one following essentially the same procedure as that described in Example 1 part (iv), and was obtained as a yellow oil. The product was characterized by proton nuclear magnetic resonance spectroscopy. Pmr spectrum (CDCl$_3$; δ in ppm): 1.00 (3H,t); 1.32 (3H,t); 1.52 (2H,m); 2.15 (3H,s); 2.17 (3H,s); 2.22 (3H, s); 2.25–3.37 (8H,m); 3.74 (1H,m); 4.11 (2H,q); 4.49 (2H,t); 15.18 (1H,broad s).

EXAMPLE 12

This non-limiting Example illustrates the preparation of formulations of the compounds of the invention.

(a) Emulsifiable Concentrate

Compound No 11 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No 11 (5 parts by weight) and "Dyapol" PT (1 part by weight) was added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade Mark and "Dyapol" PT is an anionic suspending agent; "Teric" N8 is a product of ethoxylation of nonylphenol.)

(c) Emulsifiable Concentrate

Compound No 11 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction).

(d) Dispersible Powder

Compound No 11 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

(e) High Strength Concentrate

Compound No 11 (99 parts by weight), silica aerogel (0.5 parts by weight) and synthetic amorphous silica (0.5 parts by weight) were blended and ground in a hammer-mill to produce a powder having a particle size less than 200 microns.

(f) Dusting Powder

Compound No 11 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing a surface active agent and/or oil, to give aqueous compositions of the required concentration which were used, as described in Examples 13 and 14, in the evaluation of the pre-emergence and post-emergence herbicidal activity of the compounds.

EXAMPLE 13

The pre-emergent herbicidal activity of the compounds of the invention formulated as described in Example 12 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were sprayed with the required quantity of a composition of the invention. Two duplicate seed boxes were prepared in the same manner but were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 2 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese millet
P: Peas
Ip: Ipomea
Ms: Mustard
Sf: Sunflower

TABLE 2

PRE-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 2 | 5 | 4 | 5 | 5 | 0 | 0 | 0 | 0 |
| 1 | 0.5 | 2 | 3 | 5 | 5 | 0 | 0 | 0 | 0 |
| 2 | 2 | 0 | 5 | 5 | 5 | 0 | 0 | 0 | 0 |
| 2 | 0.5 | 0 | 2 | 5 | 4 | 0 | 0 | 0 | 0 |
| 4 | 2 | 2 | 5 | 5 | 5 | 0 | 0 | 0 | 0 |
| 4 | 0.5 | 0 | 1 | 3 | 4 | 0 | 0 | 0 | 0 |
| 5 | 1.0 | 0 | 0 | 4 | 3 | 0 | 0 | 0 | 0 |
| 7 | 0.25 | 0 | 1 | 3 | 5 | 0 | 0 | 0 | 0 |
| 8 | 0.25 | 0 | 0 | 3 | 5 | 0 | 0 | 0 | 0 |
| 9 | 0.25 | 0 | 0 | 5 | 5 | 0 | 0 | 0 | 0 |

EXAMPLE 14

The post-emergent herbicidal activity of the compounds of the invention formulated as described in Example 12 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese Millet
P: Peas
Ip: Ipomea
Ms: Mustard
Sf: Sunflower

TABLE 3

POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 2 | 4 | 5 | 5 | 5 | 0 | 0 | 0 | 0 |
| 1 | 0.5 | 3 | 5 | 5 | 5 | 0 | 0 | 0 | 0 |
| 2 | 2 | 2 | 3 | 5 | 5 | 0 | 0 | 0 | 0 |
| 2 | 0.5 | 0 | 2 | 4 | 4 | 0 | 0 | 0 | 0 |
| 4 | 2 | 4 | 5 | 5 | 5 | 0 | 0 | 0 | 0 |
| 4 | 0.5 | 3 | 4 | 5 | 5 | 0 | 0 | 0 | 0 |
| 6 | 0.25 | 3 | 4 | 5 | 5 | 0 | 0 | 0 | 0 |
| 6 | 0.06 | 1 | 1 | 4 | 5 | 0 | 0 | 0 | 0 |
| 7 | 0.25 | 4 | 4 | 5 | 5 | 0 | 0 | 0 | 0 |
| 7 | 0.06 | 3 | 2 | 4 | 5 | 0 | 0 | 0 | 0 |
| 8 | 0.25 | 4 | 4 | 5 | 5 | 0 | 0 | 0 | 0 |
| 8 | 0.06 | 3 | 2 | 4 | 5 | 0 | 0 | 0 | 0 |
| 9 | 0.25 | 4 | 4 | 5 | 5 | 0 | 0 | 0 | 0 |
| 9 | 0.06 | 2 | 4 | 4 | 5 | 0 | 0 | 0 | 0 |
| 10 | 0.25 | 0 | 3 | 4 | 5 | 0 | 0 | 0 | 0 |
| 11 | 0.25 | 4 | 5 | 5 | 4 | 0 | 0 | 0 | 0 |

EXAMPLE 15

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 4 below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 4 below. A dash (-) means that no experiment was carried out.

The names of the test plants were as follows:
Sb: Sugar beet
Rp: Rape
Ct: Cotton
Sy: Soy bean
Mz: Maize
Ww: Winter wheat
Rc: Rice
Sn: Senecio vulgaris
Ip: Ipomea purpurea
Am: Amaranthus retroflexus
Pi: Polygonum aviculare
Ca: Chenopodium album
Ga: Galium aparine
Xa: Xanthium pensylvanicum
Ab: Abutilon theophrasti
Co: Cassia obtusifolia
Av: Avena fatua
Dg: Digitaria sanguinalis
Al: Alopecurus myosuroides
St: Setaria viridis
Ec: Echinochloa crus-galli
Sh: Sorghum halepense
Ag: Agropyron repens
Cn: Cyperus rotundas

TABLE 4

PART A

| Compound No | APPLICATION Method | Rate (kg/ha) | Sb | Rp | Ct | Sy | Mz | Ww | Rc | Sn | Ip | Am | Pi | Ca |
|---|---|---|---|---|---|---|---|---|---|---|---|---|---|---|
| 1 | PRE | 0.5 | — | — | — | — | 0 | 2 | 4 | — | — | — | — | — |
| 1 | PRE | 0.2 | — | — | — | — | 0 | 2 | 3 | — | — | — | — | — |
| 1 | POST | 0.5 | — | — | — | — | 4 | 4 | 4 | — | — | — | — | — |
| 1 | POST | 0.2 | — | — | — | — | 4 | 1 | 4 | — | — | — | — | — |
| 7 | POST | 0.1 | — | — | — | — | 5 | 4 | 1 | — | — | — | — | — |
| 7 | POST | 0.02 | — | — | — | — | 3 | 2 | 2 | — | — | — | — | — |
| 7 | POST | 0.01 | — | — | — | — | 2 | 0 | 0 | — | — | — | — | — |
| 8 | PRE | 0.1 | — | — | — | — | 4 | 3 | 5 | — | — | — | — | — |
| 8 | POST | 0.1 | — | — | — | — | 4 | 4 | 2 | — | — | — | — | — |
| 8 | POST | 0.02 | — | — | — | — | 2 | 0 | 2 | — | — | — | — | — |
| 9 | PRE | 0.4 | — | — | — | — | 2 | 0 | 4 | — | — | — | — | — |
| 9 | POST | 0.4 | — | — | — | — | 5 | 3 | 4 | — | — | — | — | — |
| 9 | POST | 0.1 | — | — | — | — | 3 | 3 | 4 | — | — | — | — | — |
| 9 | POST | 0.05 | — | — | — | — | 5 | 1 | 1 | — | — | — | — | — |
| 10 | PRE | 0.1 | — | — | — | — | 0 | 0 | 4 | — | — | — | — | — |
| 10 | POST | 0.1 | — | — | — | — | 5 | 1 | 3 | — | — | — | — | — |
| 10 | POST | 0.05 | — | — | — | — | 3 | 0 | 2 | — | — | — | — | — |
| 10 | POST | 0.02 | — | — | — | — | 3 | 1 | 0 | — | — | — | — | — |
| 11 | PRE | 0.2 | — | — | — | — | 3 | 3 | 5 | — | — | — | — | — |
| 11 | POST | 0.2 | — | — | — | — | 5 | 1 | 5 | — | — | — | — | — |
| 11 | POST | 0.05 | — | — | — | — | 4 | 0 | 3 | — | — | — | — | — |
| 11 | POST | 0.02 | — | — | — | — | 4 | 0 | 0 | — | — | — | — | — |

PART B

| Compound No | APPLICATION Method | Rate (kg/ha) | Ga | Xa | Ab | Co | Av | Dg | Al | St | Ec | Sh | Ag | Cn |
|---|---|---|---|---|---|---|---|---|---|---|---|---|---|---|
| 1 | PRE | 0.5 | — | — | — | — | 3 | 4 | 5 | 4 | 5 | 2 | 2 | 0 |
| 1 | PRE | 0.2 | — | — | — | — | 2 | 3 | 5 | 2 | 5 | 0 | 1 | 0 |
| 1 | POST | 0.5 | — | — | — | — | 5 | 3 | 4 | 4 | 4 | 4 | 4 | 0 |
| 1 | POST | 0.2 | — | — | — | — | 4 | 2 | 4 | 4 | 4 | 1 | 1 | 0 |
| 7 | POST | 0.1 | — | — | — | — | 4 | 5 | 4 | 5 | 5 | — | 4 | — |
| 7 | POST | 0.02 | — | — | — | — | 2 | 5 | 3 | 4 | 5 | — | 1 | — |
| 7 | POST | 0.01 | — | — | — | — | 1 | 4 | 2 | 3 | 4 | — | 0 | — |
| 8 | PRE | 0.1 | — | — | — | — | 4 | 5 | 5 | 4 | 3 | 2 | 5 | — |
| 8 | POST | 0.1 | — | — | — | — | 5 | 5 | 4 | 5 | 5 | — | 1 | — |
| 8 | POST | 0.02 | — | — | — | — | 4 | 4 | 3 | 3 | 4 | — | 1 | — |
| 9 | PRE | 0.4 | — | — | — | — | 4 | 4 | 4 | 4 | 4 | 3 | 5 | — |
| 9 | POST | 0.4 | — | — | — | — | 5 | 5 | 5 | 5 | 5 | 5 | 4 | — |
| 9 | POST | 0.1 | — | — | — | — | 4 | 4 | 4 | 4 | 5 | 5 | 2 | — |
| 9 | POST | 0.05 | — | — | — | — | 4 | 5 | 4 | 4 | 5 | 4 | 3 | — |
| 10 | PRE | 0.1 | — | — | — | — | 3 | 5 | 5 | 4 | 5 | 4 | 0 | — |
| 10 | POST | 0.1 | — | — | — | — | 4 | 4 | 3 | 4 | 4 | 4 | 0 | — |
| 10 | POST | 0.05 | — | — | — | — | 4 | 4 | 3 | 4 | 4 | 3 | 1 | — |
| 10 | POST | 0.02 | — | — | — | — | 4 | 3 | 2 | 3 | 4 | 2 | 0 | — |
| 11 | PRE | 0.2 | — | — | — | — | 5 | 5 | 5 | 5 | 5 | 4 | 5 | — |
| 11 | POST | 0.2 | — | — | — | — | 5 | 4 | 4 | 4 | 5 | 5 | 3 | — |
| 11 | POST | 0.05 | — | — | — | — | 4 | 4 | 3 | 4 | 4 | 4 | 1 | — |
| 11 | POST | 0.02 | — | — | — | — | 4 | 4 | 2 | 4 | 4 | 3 | 0 | — |

We claim:
1. A compound of formula I

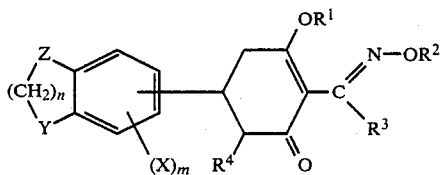

wherein:
X, which may be the same or different, are selected from the group consisting of: halogen; nitro; cyano; $C_1$ to $C_6$ alkyl; $C_1$ to $C_6$ alkyl substituted with a substituent selected from the group consisting of halogen, nitro, hydroxy, $C_1$ to $C_6$ alkoxy, and $C_1$ to $C_6$ alkylthio; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkenyloxy; $C_2$ to $C_6$ alkynyloxy; $C_2$ to $C_6$ alkanoyloxy; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, benzoyl and benzyl; the group $—C(R^7)=NR^8$ wherein $R^7$ is selected from hydrogen and $C_1$ to $C_5$ alkyl and $R^8$ is selected from the group consisting of hydrogen, $C_1$ to $C_6$ alkyl, phenyl, benzyl, hydroxy, $C_1$ to $C_6$ alkoxy, phenoxy and benzyloxy;

Y and Z are independently selected from methylene, oxygen and sulfur provided that at least one of Y and Z is selected from oxygen and sulfur;

$R^1$ is selected from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl)sulfonyl; benzenesulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_2$ to $C_6$ alkanoyl; benzoyl and substituted benzoyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; 2-furoyl; 3-furoyl; 2-thenoyl; 3-thenoyl; and an inorganic or an organic cation selected from the alkali metal ions, the alkaline earth metal ions, transition metal ions and the ammonium ion $R^9R^{10}R^{11}R^{12}N^{\oplus}$ wherein $R^9$, $R^{10}$, $R^{11}$ and $R^{12}$ are independently selected from the group consisting of: hydrogen; $C_1$ to $C_{10}$ alkyl; substituted $C_1$ to $C_{10}$ alkyl wherein the alkyl group is substituted with a substituent selected from the group consisting of hydroxy, halogen and $C_1$ to $C_6$ alkoxy; phenyl; benzyl; and the groups substituted phenyl and substituted benzyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl;

$R^4$ is selected from the group consisting of: hydrogen; halogen; cyano; $C_1$ to $C_6$ alkyl; and ($C_1$ to $C_6$ alkoxy)carbonyl;

n is an integer selected from 1 to 3; and
m is zero or an integer selected from 1 to 3.

2. A compound according to claim 1 wherein:
X, which may be the same or different, are selected from the group consisting of: halogen; nitro; cyano; $C_1$ to $C_6$ alkyl; $C_1$ to $C_6$ alkyl substituted with a substituent selected from halogen, nitro and $C_1$ to $C_6$ alkoxy; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkanoyloxy; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, benzoyl and benzyl; and the group $—C(R^7)=NR^8$ wherein $R^7$ is selected from hydrogen and $C_1$ to $C_5$ alkyl and $R^8$ is selected from the group consisting of hydrogen, $C_1$ to $C_6$ alkyl, phenyl, benzyl, hydroxy, $C_1$ to $C_6$ alkoxy, phenoxy and benzyloxy;

Y and Z are independently selected from methylene, oxygen and sulfur provided that at least one of Y and Z is selected from oxygen and sulfur;

$R^1$ is selected from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consiting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl) sulfonyl; benzene sulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_2$ to $C_6$ alkanoyl; benzoyl and substituted benzoyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; 2-furoyl; 3-furoyl; 2-thenoyl; 3-thenoyl- and an inorganic or an organic cation selected from the alkali metal ions, the alkaline earth metal ions, the transition metal ions and the ammonium ion $R^9R^{10}R^{11}R^{12}N^{\oplus}$ wherein $R^9$, $R^{10}$, $R^{11}$ and $R^{12}$ are independently selected from the group consisting of: hydrogen; $C_1$ to $C_{10}$ alkyl; substituted $C_1$ to $C_{10}$ alkyl wherein the alkyl group is substituted with a substituent selected from the group consisting of hydroxy, halogen and $C_1$ to $C_6$ alkoxy; phenyl; benzyl; and the groups substituted phenyl and substituted benzyl wherein the benzene ring is substituted with from one to three substituents selected from the group consisting of halogen, nitro, cyano, $C_1$ and $C_6$ alkyl, $C_1$ to $C_6$ haloalkyl, $C_1$ to $C_6$ alkoxy and $C_1$ to $C_6$ alkylthio;

$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl;

$R^4$ is hydrogen;

n is an integer selected from 1 to 3; and m is zero or an integer selected from 1 to 3.

3. A compound according to claim 1 wherein:

X, which may be the same or different, are selected from the group consisting of: halogen; nitro; cyano; $C_1$ to $C_6$ alkyl; $C_1$ to $C_6$ haloalkyl; $C_1$ to $C_6$ hydroxyalkyl; ($C_1$ to $C_6$ alkoxy) $C_1$ to $C_6$ alkyl; $C_1$ to $C_6$ alkoxy; $C_1$ to $C_6$ alkylthio; $C_1$ to $C_6$ alkylsulfinyl; $C_1$ to $C_6$ alkylsulfonyl; and $C_2$ to $C_6$ alkanoyl;

Y and Z are independently selected from methylene, oxygen and sulfur provided that at least one of Y and Z is selected from oxygen and sulfur;

$R^1$ is selected from the group consisting of: hydrogen; $C_2$ to $C_6$ alkanoyl; benzoyl; substituted benzoyl wherein the benzene ring is substituted with from one to three substituents selected from the group consisting of halogen, nitro, $C_1$ to $C_6$ alkyl and $C_1$ to $C_6$ alkoxy; benzenesulfonyl; substituted benzenesulfonyl wherein the benzene ring is substituted with from one to three substituents selected from the group consisting of halogen, nitro, $C_1$ to $C_6$ alkyl and $C_1$ to $C_6$ alkoxy; and an inorganic or organic cation selected from the alkali metal ions, the alkaline earth metal ions, the transition metal ions, the ammonium ion, and the tri- and tetra-(alkyl)ammonium ions wherein alkyl is selected from $C_1$ to $C_6$ alkyl and $C_1$ to $C_6$ hydroxyalkyl;

$R^2$ is selected from the group consisting of: $C_1$ to $C_6$ alkyl; $C_2$ to $C_6$ alkenyl; $C_2$ to $C_6$ alkynyl; $C_1$ to $C_6$ haloalkyl; $C_2$ to $C_6$ haloalkenyl; and $C_2$ to $C_6$ haloalkynyl;

$R^3$ is selected from $C_1$ to $C_6$ alkyl;

$R^4$ is selected from the group consisting of: hydrogen; halogen; cyano; methyl; ethyl; and ($C_1$ to $C_6$ alkoxy)-carbonyl;

n is an integer selected from 1 and 2; and m is zero or an integer selected from 1 to 3.

4. A compound according to claim 3 wherein:

X, which may be the same or different, are selected from the group consisting of: halogen; nitro; cyano; $C_1$ to $C_6$ alkyl; ($C_1$ to $C_6$ alkoxy)methyl; $C_1$ to $C_6$ alkoxy; $C_1$ to $C_6$ alkylthio; and $C_2$ to $C_6$ alkanoyl;

Y and Z are independently selected from methylene and oxygen provided that at least one of Y and Z is selected from oxygen;

$R^1$ is selected from the group consisting of: hydrogen; $C_2$ to $C_6$ alkanoyl; benzoyl; benzenesulfonyl; the alkali metal ions; the alkaline earth metal ions; the transition metal ions; the ammonium ion; and the tri- and tetra-(alkyl)ammonium ions wherein alkyl is selected from $C_1$ to $C_6$ alkyl and $C_1$ to $C_6$ hydroxyalkyl;

$R^2$ is selected from the group consisting of: $C_1$ to $C_6$ alkyl; $C_2$ to $C_6$ alkenyl; and $C_1$ to $C_6$ haloalkyl;

$R^3$ is selected from $C_1$ to $C_6$ alkyl;

$R^4$ is selected from the group consisting of: hydrogen; fluoro; cyano; and methyl;

n is an integer selected from 1 and 2; and m is zero or an integer selected from 1 to 3.

5. A compound according to claim 4 wherein:

X, which may be the same or different, are selected from the group consisting of: fluoro; chloro; bromo; nitro; cyano; methyl; ethyl; methoxymethyl; methoxy; methylthio; and acetyl;

$R^1$ is selected from the group consisting of: hydrogen; benzoyl; acetyl; pivaloyl; and the alkali metal ions;

$R^2$ is selected from the group consisting of: ethyl; 2-fluoroethyl; and allyl;

$R^3$ is selected from ethyl and n-propyl;

$R^4$ is hydrogen;

n is an integer selected from 1 and 2; and m is zero or an integer selected from 1 to 3.

6. A compound according to claim 5 wherein:

X, which may be the same or different, are selected from the group consisting of fluoro, chloro, nitro, and methyl;

$R^1$ is selected from the group consisting of hydrogen and the alkali metal ions sodium and potassium;

$R^2$ is ethyl;

$R^3$ is selected from ethyl and n-propyl;

$R^4$ is hydrogen;

n is the integer 1; and m is zero or an integer selected from 1 to 3.

7. A compound according to claim 6 of formula

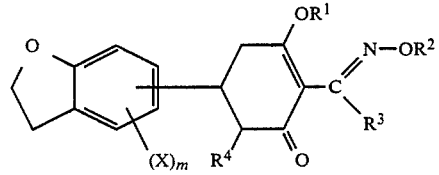

wherein:

X, which may be the same or different, are selected from chloro and methyl;

$R^1$ is selected from the group consisting of hydrogen and the alkali metal ions sodium and potassium;

$R^2$ is ethyl;

$R^3$ is selected from ethyl and n-propyl;

R⁴ is hydrogen; and m is the integer 3.

8. A compound according to claim 7 selected from the group consisting of:

2-[1-(ethoxyimino)propyl]-5-(2,3-dihydro-4,5,7-trimethylbenzo[b]furan-6-yl)-3-hydroxycyclohex-2-en-1-one;

2-[1-(ethoxyimino)propyl]-5-(2,3-dihydro-4,6,7-trimethylbenzo[b]furan-5-yl)-3-hydroxycyclohex-2-en-1-one;

2-[1-(ethoxyimino)butyl]-5-(2,3-dihydro-4,6,7-trimethylbenzo[b]furan-5-yl)-3-hydroxycyclohex-2-en-1-one;

5-(7-chloro-2,3-dihydro-4,5-dimethylbenzo[b]furan-6-yl)-2-[1-(ethoxyimino)propyl]-3-hydroxycyclohex-2-en-1-one;

5-(2,3-dihydro-5,6,7-trimethylbenzo[b]furan-4-yl)-2-[1-(ethoxyimino)butyl]-3-hydroxycyclohex-2-en-1-one; and 5-(2,3-dihydro-4,5,6-trimethylbenzo[b]furan-7-yl)-2-[1-(ethoxyimino)butyl]-3-hydroxycyclohex-2-en-1-one.

9. A herbicidal composition comprising as active ingredient a herbicidally effective amount of a compound as defined according to claim 1 and a carrier therefor.

10. A process for severely damaging or killing unwanted plants which process comprises applying to said plants, or to the growth medium of said plants, an effective amount of a compound as defined according to claim 1.

11. A process for selectively controlling the growth of monocotyledonous weeds in dicotyledonous crops which process comprises applying to said crop, or to the growth medium of said crop, a compound as defined according to claim 1 in an amount sufficient to severely damage or kill said weeds but insufficient to substantially damage said crop.

12. A process according to claim 10 or claim 11 wherein the compound is applied at a rate in the range of from 0.005 to 20 kilograms per hectare.

* * * * *